United States Patent [19]

Chen et al.

[11] Patent Number: 5,013,423

[45] Date of Patent: May 7, 1991

[54] REFORMING AND DEHYDROCYCLIZATION

[75] Inventors: Nai Y. Chen, Titusville; Ralph M. Dessau, Edison; Randall D. Partride, W. Trenton, all of N.J.; Ernest W. Valyocsik, Yardley, Pa.

[73] Assignee: Mobil Oil Corporation, Fairfax, Va.

[21] Appl. No.: 295,959

[22] Filed: Jan. 11, 1989

Related U.S. Application Data

[63] Continuation-in-part of Ser. No. 230,729, Aug. 4, 1988, abandoned, which is a continuation of Ser. No. 122,089, Nov. 17, 1987, abandoned, and a continuation of Ser. No. 138,463, Dec. 28, 1987, abandoned, and a continuation of Ser. No. 138,474, Dec. 28, 1987, abandoned, and a continuation of Ser. No. 138,472, Dec. 28, 1987, abandoned.

[51] Int. Cl.$^5$ .................. C10G 35/06; C07C 12/02
[52] U.S. Cl. .................. 208/64; 208/65; 208/134; 208/138; 585/415; 585/417; 585/419
[58] Field of Search .............. 585/415, 417, 419; 208/64, 65, 134, 138

[56] References Cited

U.S. PATENT DOCUMENTS

| | | | |
|---|---|---|---|
| 3,702,293 | 11/1972 | Hayes et al. | 208/139 |
| 3,702,294 | 11/1972 | Rausch | 208/139 |
| 3,878,131 | 4/1975 | Hayes et al. | 208/139 |
| 4,104,320 | 8/1978 | Bernard et al. | 260/673.5 |
| 4,175,031 | 11/1979 | Antos | 208/138 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,652,689 | 3/1987 | Lambert et al. | 208/138 |
| 4,867,864 | 9/1989 | Dessau | 208/138 |

FOREIGN PATENT DOCUMENTS

| | | |
|---|---|---|
| 0107389 | 4/1984 | European Pat. Off. |
| 2033358 | 5/1980 | United Kingdom |
| 2114150 | 8/1983 | United Kingdom |

OTHER PUBLICATIONS

G. Wengui et al., "IR Study of Framework Vibrations and Surface Properties of High Silica Zeolites", Zeolites, Elsevir Science, Amsterdam, 1985, p. 279.

Ione, Journal of Molecular Catalysis, 31, pp. 355-370 (1985).

Ione, "Structure and Reactivity of Modified Zeolites", Elsevir Science, (1984), pp. 151-155.

*Primary Examiner*—Curtis R. Davis
*Attorney, Agent, or Firm*—Alexander J. McKillop; Charles J. Speciale; Marina V. Schneller

[57] ABSTRACT

Improved, dehydrocyclization and low-pressure reforming processes based on a non-acidic metal containing crystalline microporous indium catalyst, in which the feed is rich in $C_6$–$C_7$ low octane hydrocarbons, such as paraffins, and in which the reformate has increased aromatic content and increased octane value over that of the feed are disclosed.

66 Claims, 1 Drawing Sheet

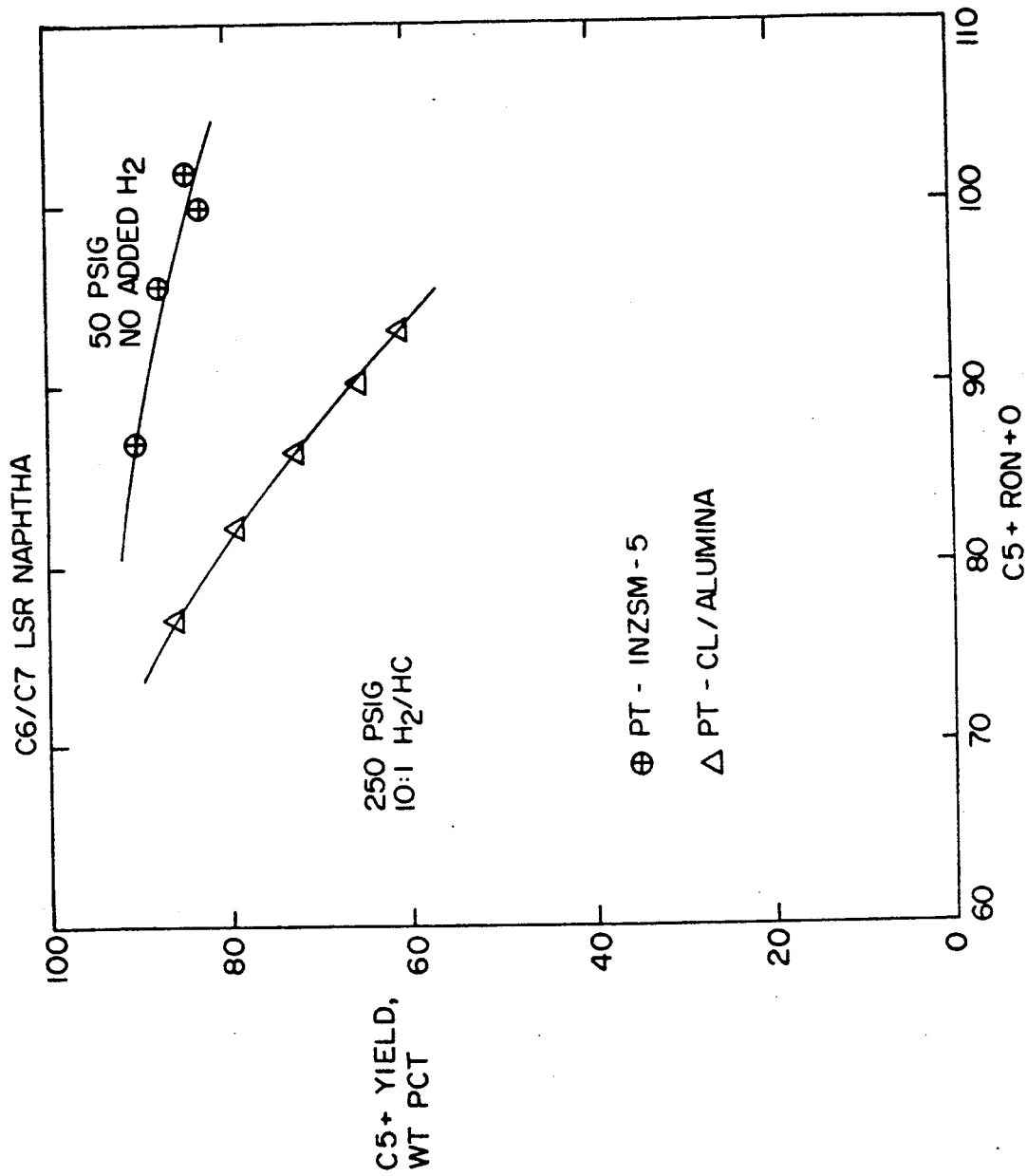

REFORMING AND DEHYDROCYCLIZATION

CROSS-REFERENCE TO RELATED APPLICATIONS

This application is a continuation-in-part of Ser. No. 230,729 filed on Aug. 4, 1988, which in turn is a continuation (Rule 62) of Ser. No. 122,089 filed Nov. 17, 1987; of Ser. No. 138,463 filed Dec. 28, 1987; of Ser. No. 138,474 filed Dec. 28, 1987; and of Ser. No. 138,472 filed Dec. 28, 1987 all of which are now abandoned. Each of said applications is relied upon and incorporated by reference herein.

FIELD OF THE INVENTION

This invention relates to the manufacture of benzene and toluene from normal hexane and normal heptane. The invention also relates to catalytic reforming of naphthas having low octane values to increase that octane value. The catalyst comprises a non-acidic platinum indium containing crystalline microporous material. A result of the catalytic process of the invention is an increase in liquid yields by minimizing, if not eliminating, the cracking of $C_{5+}$, hydrocarbons which include $C_6$ and $C_7$ paraffins.

The invention further allows improving reforming to maximize yields and octane increase of the reformate by decreasing the partial pressure of hydrogen, an off gas or byproduct of reforming, in the reforming unit and employing as the reforming catalyst, a non-acidic indium containing crystalline microporous material combined with reforming hydrogenation/dehydrogenation metal, such as platinum.

The invention further includes catalytic treatment of a reformate high in $C_{5+}$ paraffin content and of low octane. The catalyst used is a non-acidic indium containing crystalline microporous material, containing a hydrogenation/dehydrogenation metal. That $C_{5+}$ paraffin component of the feed is converted to aromatic components of higher octane value thereby increasing the octane rating of the reformate.

BACKGROUND OF THE INVENTION

Very large amounts of benzene and toluene are consumed annually. These materials find use as chemical intermediates, solvents, and in gasoline.

By far the largest proportion of the available benzene and toluene is made in petroleum refining by the so-called (petroleum naphtha) reforming process. This process is so well known that it need not be described in detail here. Briefly, one of the major reactions in catalytic reforming is the isomerization and dehydrogenation of five and six-membered naphthene compounds contained in the naphtha to form a mixture of benzene, toluene, and xylene which materials can be recovered by distillation and solvent extraction as a mixture commonly referred to as "BTX". This mixture can be resolved by distillation to provide merchant benzene, toluene, and mixed xylenes for further use.

The statutory elimination of lead from most gasolines has compelled refiners to rely heavily on hydrocarbon conversion processes that produce gasoline blending stocks having a high octane number even without the inclusion of lead. Two principal processes for accomplishing this are alkylation and reforming, which produce such high octane blending stocks for the lead-free gasolines. Accordingly, refiners who rely heavily on reforming for gasoline production are understandably reluctant to allow the reformate product to be stripped of the high octane aromatics. There results from this situation a decrease in the available supply of benzene and toluene and a concomitant increase in their cost. There is an evident growing need for alternative methods to manufacture benzene and toluene, methods which do not rely on reformate as the principal source.

Catalytic reforming is a process in which hydrocarbon molecules are rearranged, or reformed in the presence of a catalyst. The molecular rearrangement results in an increase in the octane rating of the feedstock. Thus, during reforming low octane hydrocarbons in the gasoline boiling range are converted into high octane components by dehydrogenation of naphthenes and isomerization, dehydrocyclization and hydrocracking of paraffins.

By way of illustration, the significance of those reactions in reforming can be gleaned from a review of the following table from "Catalysis," vol VI, P. H. Emmett (ed). Copyright 1958 by Litton Educational Publishing Company:

| Octane Numbers of Pure Hydrocarbons | |
|---|---|
| Hydrocarbon | Blending research octane number (clear) |
| Paraffins: | |
| n-Butane | 113 |
| n-Pentane | 62 |
| n-Hexane | 19 |
| n-Heptane | 0 |
| n-Octane | −19 |
| 2-Methylhexane | 41 |
| 2,2-Dimethylpentane | 89 |
| 2,2,3-Trimethylbutane | 113 |
| Naphthenes (cycloparaffins): | |
| Methylcyclopentane | 107 |
| 1.1-Dimethylcyclopentane | 96 |
| Cyclohexane | 110 |
| Methylcyclohexane | 104 |
| Ethylcyclohexane | 43 |
| Aromatics: | |
| Benzene | 99 |
| Toluene | 124 |
| 1,3-Dimethylbenzene | 145 |
| Isopropylbenzene | 132 |
| 1,3,5-Trimethylbenzene | 171 |

Naphtha reforming may also be utilized for the production of benzene, toluene, ethylbenzene, and xylene aromatics. A valuable by-product of naphtha reforming is hydrogen, which may be utilized for hydrotreating and upgrading of other hydrocarbon fractions. Generally, the molecular rearrangement of molecular components of a feed, which occurs during reforming, results in only slight, if any, changes in the boiling point of the reformate (the product of reforming), compared to that of the feed. Accordingly, reforming differs from both cracking and alkylation, both refinery processes, each of which does result in changes of boiling range of the product compared to the feed. That is, in cracking, large molecules are cracked into smaller ones; whereas, in alkylation small molecules are rebuilt into larger molecules.

The most important uses of the reforming process are briefly mentioned: the primary use of catalytic reforming may be concisely stated to be an octane upgrader and a route to premium gasoline. Catalytic reforming is the only refining process that is capable of economically making a gasoline component having high clear research octane ratings. The charge to the reformer (straight-run, thermal, or hydrocracker naphtha) is usually available in large quantities and is of such low quality that most of it would be unsaleable without reforming.

A correlative use of catalytic reforming is in its ability to produce gasolines of acceptable volatility over a wide range of yields, through proper selection of feedstock and/or operating conditions. The refiner is thus able to vary the yield of gasoline very substantially to meet demand fluctuations. For European demand patterns, where gasoline sales are limiting and it is desired to produce as much middle distillate as practicable, the reformer can be operated on a lighter, lower volume of naphtha to minimize gasoline production while maintaining high crude runs.

Hydrogen, although often considered a by-product, is still a valuable output from the reformer. Normally, it is produced in amounts ranging from 300 to 1200 SCF/Bbl, depending on the type of feed stock and reformer operating conditions. Reformer hydrogen is used to remove unwanted contaminants from reformer feed stocks, for hydrodesulfurization of distillates, hydrocracking of heavy fractions, hydrotreating of lubes and various chemical operations. Hydrogen availability and utilization is expected to assume increasing importance as pollution restrictions lead to increasing hydroprocessing in future years.

The importance of reforming is reflected by data which indicates that finished pool gasoline is about 35% reformate in complex refineries, but can run as high as 80% in topping-reforming refineries. As lead is phased out of gasoline, more and more straight run stocks which are now blended directly into gasoline will be reformed. All current commercial reformers use a platinum containing catalyst with a hydrogen recycle stream. Within this broad definition, there are a great number of different process designs. More than 75% of the industry's reforming capacity is classified as semi regenerative. A semi-regenerative reformer is one which runs until the catalyst is coked and then is shut down and regenerated. The time period between regenerations varies from several months to as long as 1½ years.

Within the category of semi-regenerative reforming, a further breakdown can be made on the basis of operating pressure. Units with separator pressures of 450 psig or higher are considered high pressure units. Those with pressures of 300 psig or less are called low pressure units. Anything in between is intermediate pressure. Most of the older units are high pressure, while the newer designs are low or intermediate pressure. Lower pressures give better reformate yields at a given octane level.

Another type of reformer is the cyclic variety. A cyclic unit has the reactors manifolded in such a way that any reactor can be taken out of reforming service and regenerated while the other reactors are still reforming. The time period between regenerations for a cyclic reactor varies from 2 to 10 days. All cyclics are low pressure.

A third type of reformer that has recently been commercialized is the continuous unit. In this type of reformer, catalyst is withdrawn from the unit during reforming, regenerated in small batches in separate regeneration facilities and then replaced in the unit. The regeneration period for continuous units is about one month. As in the case for cyclic units, all continuous units are low pressure.

The reformer is run to operate at a given octane for the reformate, under adiabatic conditions. Thus, the unit can be run at low octane severity or at high octane severity. By way of explanation, it is noted that in the semi-regenerative process comprising several manifolded units the reformate from the last of the units will be characterized by the desired octane, while that product of the preceding manifolded units will be of successively lower octane. Because of both thermodynamics and kinetics of reforming, cracking, if it occurs, predominates at the end of the reforming operation particularly in the semi-regenerative process (i.e. in the last of three units) and in the continuous process. Cracking of long chain paraffins of low octane value (which decrease the final octane of the reformate) results in decreased liquid yields. The cracking of such paraffins results in products outside the boiling range of the reformate. It also results in deactivation of the catalyst, e.g. by coking and deposit of carbonaceous matter other than coke on the catalyst, in a way that is not attributable to the other reactions occurring during reforming. In the semi regenerative and continuous reforming processes, cracking would predominate in the last unit.

Prior to about 1950 chromium oxide or molybdenum oxide supported on alumina were used to effect the two functions of a reforming catalyst. The hydrogenation-dehydrogenation function for paraffin olefin conversion during reforming is effected by the metals chromium and molybdenum and more recently platinum, rhenium, admixtures thereof and noble-metal containing trimetallic alloys. Isomerization activity was provided by acidified alumina.

From the commercialization of platinum reforming in the middle 1950's to the late 1960's, there were no significant improvements in reforming catalysts.

In the late 1960's a dramatic breakthrough in reforming catalysts occurred. This was the introduction of the platinum-rhenium bimetallic catalysts. These catalysts have greatly improved stability compared to platinum-only catalysts. By way of background, the platinum and platinum bimetallic catalysts were generally supported on carriers.

Recently, the patent literature has started to recognize the use of platinum and non-shape selective zeolite containing catalyst compositions in reforming. For example, that is the zeolite may replace in whole or in part the function of alumina in prior reforming catalysts. U.S. Pat. No. 4,456,527 describes zeolite L as a component in a composition for catalyzing reforming.

Zeolites include naturally occurring and synthetic zeolites. They exhibit catalytic properties for various types of hydrocarbon conversions. Zeolites are porous crystalline aluminosilicates having definite crystalline structure as determined by X-ray diffraction studies. Such zeolites have pores of uniform size which are uniquely determined by unit structure of the crystal. The zeolites are re(erred to as "molecular sieves" because interconnecting channel systems created by pores of uniform pore size allow a zeolite to selectively absorb molecules of certain dimensions and shapes.

By way of background, one authority has described the zeolites structurally, as "framework" aluminosilicates which are based on an infinitely extending three-dimensional network of $AlO_4$ and $SiO_4$ tetrahedra linked to each other by sharing all of the oxygen atoms. Furthermore, the same authority indicates that zeolites may be represented by the empirical formula $M_{2/n}O.Al_2O_3.xSiO_2.yH_2O$ In the empirical formula, x is equal to or greater than 2, since $AlO_4$ tetrahedra are joined only to $SiO_4$ tetrahedra, and n is the valence of the cation designated m. D. Breck, ZEOLITE MOLECULAR SIEVES, John Wiley & Sons, New York p.5 (1974). In the empirical formula, the ratio of the total of silicon and aluminum atoms to oxygen atoms is 1:2. M was described therein to be sodium, potassium, magnesium, calcium, strontium and/or barium, which complete the electrovalence makeup of the empirical formula.

The prior art describes a variety of synthetic zeolites. These zeolites have come to be designated by letter or other convenient symbols, as illustrated by the zeolite. The silicon/aluminum atomic ratio of a given zeolite is often variable. Moreover, in some zeolites, the upper limit of the silicon/aluminum atomic ratio is unbounded. ZSM-5 is one such example wherein the silicon/aluminum atomic ratio is at least 2.5 and up to infinity. U.S. Pat. No. 3,941,871, reissued as U.S. Pat. No. 29,948, discloses a porous crystalline silicate made from a reaction mixture containing no deliberately added aluminum and exhibiting the X-ray diffraction pattern characteristic of ZSM-5. Various patents describe inclusion of elements other than silicon and aluminum in the preparation of zeolites. Cf. U.S. Pat. No. 3,530,064, U.S. Pat. Nos. 4,208,305 and 4,238,318 describe the preparation of silicates in the presence of iron.

Zeolites may be classified by pore size. ZSM-5 is a member of a class of zeolites sometimes referred to as medium pore zeolites. The pore sizes of medium pore zeolites range from about 5 to about 7 Angstroms.

Another class of zeolites sometimes referred to as large pore zeolites include inter alia naturally occurring faujasite, synthetic zeolites X,L,Y and zeolite beta. These zeolites are characterized by pore sizes greater than those of the medium pore zeolites. The pore sizes of large pore zeolites are greater than about 7 Angstroms. Because of the larger pore sizes these latter zeolites may be less (molecule) shape selective.

SUMMARY OF THE INVENTION

The invention provides a process for manufacturing benzene, toluene, or mixtures thereof which comprises contacting under dehydrocyclization conditions a feed comprising substantially isomer-free normal hexane or normal heptane or a mixture thereof with a non-acidic dehydrocyclization catalyst comprising a platinum group metal, a crystalline microporous silicate exhibiting the X-ray diffraction pattern of a zeolite and indium modifier.

In accordance with the invention, naphthas rich in $C_6$ and $C_7$ paraffins, difficult to reform selectively using conventional catalysts, are reformed over compositions containing a reforming metal and crystalline microporous non-acidic indium containing materials. The reformate produced thereby is characterized by higher net yield of aromatic gasoline than would result from reforming in the presence of conventional reforming catalysts.

The invention further relates to improvements in reforming naphthas in the presence of the new reforming catalyst comprising a reforming metal and a non-acidic crystalline microporous material containing indium by decreasing the hydrogen partial pressure in the reforming unit. This is accomplished by the introduction of a diluent stream to reduce the hydrogen partial pressure throughout the reactor.

In accordance with the invention, a low octane severity reformate feedstock can be contacted with said catalyst comprising a hydrogenation/dehydrogenation component and a non-acidic indium containing microporous crystalline material capable of converting $C_{6+}$ paraffins in the feedstock to $C_{6+}$ aromatics. In one embodiment of the invention a naphtha feedstock is subjected to reforming conditions effective to produce a reformate having a research octane of 50 to 90, and then that reformate of 50-90 research octane is contacted with the catalyst comprising the hydrogenation/dehydrogenation component and said non-acidic indium containing microporous crystalline material, under conditions to effect the aromatization of the paraffins in the feedstock to increase the treated reformate's octane value. This two stage process will result in overall increased liquid yields, compared to conventional reforming processes run to a given octane which result in cracking (or hydrocracking) of the $C_{6+}$ paraffins.

DESCRIPTION OF THE DRAWINGS

The Figure is a graph of the plot of $C_5{}^+$ yield in weight per cent vs. $C_5{}^+$ RON+O.

DETAILED DESCRIPTION OF THE INVENTION

The Feedstocks

The feed for the process of this invention which relates to benzene and toluene production comprises substantially isomer-free normal hexane or normal heptane or mixtures thereof. The phrase "isomer-free" as used herein means free of isomeric paraffins, e.g., isomer-free normal hexane would be substantially free of 2-methyl and 3-methylpentane, and also free of 2,2-dimethyl and 2,3-dimethyl butane.

The substantially isomer-free normal hexane or normal heptane is obtainable from a distillation cut of natural gasoline. Suitable methods for separating the normal paraffins such as superfractionation, urea adduction, and bulk separation by Type 5A molecular sieve may be used. Such methods are known and need not be described herein in detail. The preferred method for use in this invention is molecular sieve separation. Several such processes are in commercial use for the recovery of normal paraffins from refinery streams. During the adsorption step of such separation, the effluent contains isoparaffins and cyclic hydrocarbons. High purity normal paraffins are recovered by desorption or by displacement with a lighter normal paraffin such as propane. Not more than about 5 wt %, and preferably not more than 2.5 wt %, of isoparaffins and cyclic compounds should be present in the feed. The normal hexane, heptane or mixture thereof should constitute at least about 90 wt % of the total $C_{5+}$ hydrocarbons in the feed, and preferably about 95 wt %. The normal hexane, heptane or mixture thereof is recovered by Type 5A molecular sieve separation using propane as desorbent, and the desorbed effluent containing propane is catalytically converted without prior separation of propane. Reduction of the partial pressure of the benzene and/or toluene product by propane favors its formation.

In addition to the isomer-free normal paraffins, the feed may contain a diluent such as hydrogen, an inert gas such as nitrogen, or an aliphatic hydrocarbon containing less than five carbon atoms. It is a feature of this invention that the conversion takes place with high selectivity and slow catalyst aging even in the absence of added hydrogen. However, the presence of a small amount of hydrogen may be used to further slow the aging, but some loss of catalyst activity may accompany its use. When hydrogen is used, it is preferred that it be used in conjunction with an inert gas or other hereinabove described diluent.

The conversion conditions for benzene and toluene production are noted in Table I.

TABLE 1

| | Conversion Conditions | | |
|---|---|---|---|
| | Temperature | WHSV $C_6$-$C_7$ | Total Pressure (Abs.) |
| Broad | 400° to 600° C. | 0.1 to 10.0 | 5 to 500 psi |
| Preferred | 450° to 550° C. | 0.3 to 2.5 | 15 to 150 psi |

The WHSV (weight hourly space velocity) in Table I refers to the hexane and/or heptane component of the feed, and the total pressures given are absolute pressures.

The use of normal hexane and normal heptane substantially free of isomers, and a feed substantially free of cyclic compounds such as methyl and dimethyl cyclopentane, fosters long catalyst life and relatively infrequent regeneration.

The feedstock charge to the new reforming process can be straight-run, thermal, or catalytically cracked naphtha. Typically, naphthas boil at 80° to 400° F. Preferably, for high increases in the aromatic content and high octane numbers of the reformate, the charge to the reformer is a naphtha rich in $C_6$ to $C_{10}$ paraffins; these are generally difficult to reform selectively using conventional catalysts (such as chlorided Pt-alumina).

Naphtha fractions boiling below 150° F., which contain pentanes and methylpentanes, are preferably taken as gasoline by blending or processed separately. The higher boiling fractions, for example, 150°-400° F. which contain $nC_{6+}$ paraffins are processed at reforming conditions over the catalyst used in this invention. In another embodiment, this naphtha is separated into fractions, at least one of which is processed.

For example, the 180°-250° F. light naphtha fraction containing $nC_6$-$C_7$ paraffins is processed over the indium containing catalyst. This flight naphtha fraction is difficult to convert selectively to aromatics over traditional dual functional reforming catalysts, where paraffin isomerization and hydrocracking reactions compete. The remaining 250° F. fraction can be processed over conventional reforming catalyst with yield and/or octane gains greater than that obtained by conventional reforming alone.

The naphtha fractions may be hydrotreated prior to reforming; but hydrotreating is not necessarily required when using the catalyst in accordance with the invention.

Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphtha fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between about 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon. The catalyst may be any of the known hydrotreating catalysts, many of which are available as staple articles of commerce. These hydrotreating catalysts are generally metals or metal oxides of Group VIA and/or Group VIII deposited on a solid porous support, such as silica and/or metal oxides such as alumina, titania, zirconia or mixtures thereof. Representative Group VIA metals include molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent.

Reformates are produced by reforming straight-run, thermal or catalytically cracked naphthas. Preferably, the reformates used in the post reforming treatment of the invention have research octane numbers of 50 to 90, and are thus low octane severity reformates. Most preferably, the research octane numbers of the reformate feed is 70 to 90. In such reformates (of 50 to 90 research octane) little if any hydrocracking of $C_6$ and $C_7$ paraffins contained therein has occurred. Reforming of $C_6$ and $C_7$ paraffins is most difficult. In other terms, preferably the naphtha precursor of the reformate is preferably a paraffinic naphtha containing $C_6$-$C_7$ paraffins.

Reforming and Post-Reforming Process Conditions

Reforming of the naphtha fraction to produce the reformates of 50 to 90 octane is undertaken by conventional reforming in semi-regenerative, cyclic or continuous units. Process conditions in reforming include pressures up to 500 psig; temperatures of 800° F. to 1100° F.; unit inlet $H_2$/HC molar ratios of 1 to 20 and LHSV of 0.1 to 20.0. Conventional reforming catalysts can be used. To produce low octane severity reformates, naphtha catalyst contact time and/or reaction temperature is reduced during reforming. That contact time can be reduced by decreasing the amount of catalyst which would be used in a unit lined-out to produce reformate of given octane. Alternatively, LHSV of the feed can be increased over that in the lined-out unit. Alternatively, if 3 units are manifolded as in the semi-regenerative process, product can be diverted after the second unit to by-pass the third unit. Conventional reforming catalysts are chlorided; generally, they are presulfided and used on feeds containing less than about 5 ppm sulfur, and preferably less than 1 ppm. They are often run on systems exhibiting low water (vapor) partial pressures. These catalysts can be platinum on alumina chlorided and presulfided run at low water vapor partial pressures; platinum rhenium chlorided and run at low water (vapor) pressures; trimetallics on alumina in which each of the trimetallic components is selected from the group consisting of platinum, rhenium, iridium, and rhodium or platinum and tin on alumina, chlorided and run at low water vapor partial pressures.

When reforming is undertaken over the indium catalyst in accordance with the invention, the temperature of reforming in accordance with the invention can range from 800° F. to 1100° F., generally being greater than about 900° F., preferably 900° F. (482° C.) to 1050° F.; the pressure will be from about 1 atmosphere to 500 psig, preferably from 30 psig to 250 psig; inlet $H_2$/hydrocarbon can be 10 or less, even zero (0) as discussed in the Examples (because of hydrogen production during reforming, there will be a hydrogen partial pressure in the unit); while the LHSV (liquid hourly space velocity) can be 0.1 to 20, preferably 0 1 to 10.

In one embodiment of the invention, reforming of the heavy naphtha fraction, boiling range of up to 400° F. is undertaken separately from the light naphtha fraction, by conventional reforming. As discussed above, conventional reforming may be semi-regenerative, cyclic or continuous. Process conditions in conventional reforming include pressures of about 0 to 500 psig, preferably, the pressures used herein range from 50-250 psig; temperatures of 800° to 1100° F.; $H_2$/HC molar ratios of 1 to 20:1 preferably of about 2:1 to about 6:1; LHSV of 0.1 to 20 hr$^{-1}$. Conventional reforming catalysts for this stage can include conventional reforming hydrogenation/dehydrogenation metals on aluminas. Those reforming hydrogenation/dehydrogenation metals include: platinum, platinum-rhenium; platinum with iridium, rhenium, rhodium or admixtures thereof; or platinum/tin. These hydrogenation/dehydrogenation metal combinations are on alumina and are chlorided; generally they are presulfided prior to use on feeds containing less than about 1 ppm sulfur.

Reduction of the hydrogen partial pressure in the reforming process of the invention comprises adding a stream of a non-hydrogen diluent, as a cofeed, inert in that it (the diluent) does not react directly to form aromatics, rather it is inert to aromatization which occurs under the conditions of the process.

The diluents can be helium, nitrogen, carbon dioxide, and light hydrocarbons through $C_5$ such as methane, ethane, propane, butane, pentane, ethylene, propylene, butenes, pentenes and mixtures thereof. The use of $C_3$-$C_5$ hydrocarbons as cofeeds may be particularly desirable in that they can be easily separated from the hydrogen produced in the aromatization reactions. The diluent may also be recycle of part or all of the aromatic rich reformate. Accordingly, the diluents can constitute aromatic compounds.

The diluent to hydrocarbon feed molar ratio can range from 1 to about 20 with best results obtained in the range of about 2:1 to 10:1.

In accordance with the post reforming treatment of the invention, reformates having research octane of 50 to 90 includes subjecting that reformate to elevated temperature conditions in the presence of catalyst composition comprising a hydrogenation/dehydrogenation component and non-acidic indium microporous material described below.

In accordance with the invention, the post reforming treatment includes temperatures of at least about 800° F., ranging from 800° F. to 1100° F., generally greater than about 900° F., preferably 900° F. (482° C.) to 1050° F.; the pressure will be from about 1 atmosphere to 500 psig, preferably from 30 psig to 250 psig; inlet $H_2$/hydrocarbon (feedstock) ratios can be 10 or less, even zero (0) as discussed in the Examples (because of hydrogen production during reforming, there will be a hydrogen partial pressure in the unit); while the LHSV (liquid hourly space velocity) can be 0.1 to 20, preferably it is 0.1 to 10.

Catalyst of the Invention

The catalyst of the invention is a two component catalyst comprising a hydrogenation/dehydrogenation component and an indium containing non-acidic crystalline microporous material. Preferably, that material is a crystalline microporous indium silicate. The hydrogenation/dehydrogenation component can be those including a platinum group metal; platinum-rhenium; platinum with iridium, rhenium, rhodium or mixtures thereof; but preferably, it is platinum. These are also referred below as reforming hydrogenation/dehydrogenation metals.

The amount of the reforming metal in the catalyst composition can rane from 0.01 to 30 weight percent and preferably from 0.02 to 10 weight percent and most preferably from 0.05 to 5 weight percent.

The indium content of the crystalline materials can range from 0.01 to 20 weight percent. Practically, the indium content will range from 0.1 to 10 weight percent.

The crystalline indium containing materials of the invention include zeolites characterized by Si/Al ratios of at least 2. However, the silica:alumina ratio of the zeolite can be up to 1000, or greater. In specific embodiments the aluminum content of some of these materials is less than 0.1 weight percent.

The crystalline indium containing material of the invention can contain other elements including boron, iron, chromium and gallium. The content of these other elements in the crystalline indium containing materials can range from 0 to 10 weight percent.

The indium containing precursors of the invention, described herein, are crystalline in the sense that they are identifiable as isostructural with zeolites by X-ray powder diffraction pattern.

The crystalline microporous indium containing material has an X-ray diffraction pattern which corresponds to a zeolite, SAPO, ALPO, etc. For example, indium silicate compositions of the invention have been made the crystal structure of which is that of ZSM-5, ZSM-11, ZSM-12 ZSM-23, ZSM-48, ZSM-50, zeolite Beta, ZSM-20, and SAPO-5; and the X-ray diffraction pattern and significant lines Tables of these materials have been described in the U.S. Patent literature; these are characterized by pore sizes up to about 8 Angstroms. In a preferred embodiment the pore size of the microporous crystalline indium containing silicates ranges from about 5 to about 8 Angstroms.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1. Small pore: n-$C_6$/i-$C_6$ sorption ratio greater than approximately 10.
2. Medium pore: n-$C_6$/i-$C_6$ is less than 10 and n-$C_6$/Mesitylene sorption ratio greater than approximately 5.
3. Large pore: n-$C_6$/Mesitylene sorption ratio less than approximately 5.

The compositions comprising hydrogenation/ dehydrogenation metal combined with the crystalline indium containing materials do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between and 10 and 60%. Alternatively, the non-acidic compositions will exhibit a pH of at least 6 when added to distilled deionized pH7 water maintained under inert (such as argon) atmosphere; by an inert atmosphere in this context it means an atmosphere free of $CO_2$. Typically, in these tests, 100 mg of catalyst was added to 30 ml. of distilled deionized water. Some compositions will exhibit a pH of at least 7.5.

When, as in embodiments herein, the crystalline indium dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison indium-free counterparts of those compositions catalyzed also hydrogenolysis of paraffins, e.g., to methane, as a major competing side reaction; and, accordingly, the latter compositions exhibit decreased selectivity for the aromatization of paraffins but increased selectivity for $C_1$-$C_5$ paraffin production. Some of the aforementioned catalysts were screened for hexane and heptane aromatization at 538° C. in the presence of nitrogen diluent. The results are shown in Table A below in which the crystalline silicate employed exhibited the diffraction pattern of a ZSM-5.

TABLE A

| Paraffin Aromatization over Pt/ZSM-5 | | | | | |
|---|---|---|---|---|---|
| Support | Paraffin | Conversion | Benz. Sel.[c] | Tol. Sel. | C5-Sel |
| B/ZSM-5 | n-hexane | 52% | 31% | — | 12%[a] |
| " | " | 98% | 51% | 2% | 40%[a] |

TABLE A-continued

| Paraffin Aromatization over Pt/ZSM-5 | | | | | |
|---|---|---|---|---|---|
| Support | Paraffin | Conversion | Benz. Sel.[c] | Tol. Sel. | C5-Sel |
| " | heptane | 56% | 56% | 8% | 7%[a] |
| " | " | 95% | 33% | 31% | 34%[a] |
| In/ZSM-5 | n-hexane | 60% | 81% | — | 1% |
| " | " | 99+% | 95% | — | 4% |
| " | heptane | 50% | — | 92% | 1% |
| " | " | 99% | — | 97% | 1% |
| Si/ZSM-5[b] | n-hexane | 58% | 69% | — | 18%[a] |
| " | " | 99% | 72% | — | 26%[a] |
| " | heptane | 34% | 45% | 17% | 14%[a] |
| " | " | 99% | 62% | 4% | 34%[a] |

[a] primarily methane.
[b] high silica/alumina ZSM-5.
[c] $H_2$-free selectivity based on carbon The non-acidic platinum catalyst prepared from In/ZSM-5 provided much higher aromatics selectivity than all the other catalysts examined. Benzene yields from hexane were as high as 95%, while heptane produced toluene in 97% yield ($H_2$ free carbon base).

The other catalysts, including Pt/B-ZSM-5 and Pt/high silica:alumina ratio did not show any appreciable acid activity, in that platinum chemistry dominated. Significant metal-catalyzed aromatization was observed; however hydrogenolysis to methane constituted a major competing side reaction. The highest toluene selectivity observed was 50-55%, and in most cases that selectivity was significantly lower. This is in sharp contrast to the aromatic product selectivity of the platinum-/In/ZSM-5. The cause for this difference in platinum behavior from the Pt/In-ZSM-5 catalyst is not clear. By way of comparison and illustration, it is noted that over dual functional platinum on acidic alumina reforming catalysts, the rate of heptane cracking to $C_{6-}$ was twice the rate of dehydrocyclization. Cf J. H. Sinfelt, "Bimetallic Catalysts", J. Wiley, New York; p. 141 (1983).

Synthesis of the Crystalline Microporous Indium Containing Compositions

The crystalline indium-materials can be made in various ways. Indium incorporation can be during synthesis or post-synthesis; and the materials can be prepared either by stepwise or simultaneous incorporation of the indium and the hydrogenation/dehydrogenation function. The dehydrogenation function can be first introduced to the synthesis product with subsequent indium incorporation, or vice versa. Stepwise preparation includes techniques of cocrystallization, impregnation, or exchange. Crystallization can be undertaken in a two phase system described in commonly assigned Ser. No. 878,555, filed June 26, 1986. Other elements such as boron, iron chromium, gallium, can also be included. Simultaneous incorporation includes the combination of indium with the dehydrogenation/hydrogenation function during synthesis (i.e., crystallization) or simultaneously after synthesis of the crystalline material.

An indium free material can be treated with indium compounds at elevated temperatures. Such treatments can be conducted so that the source of indium is either in the gaseous (such as indium chloride) or the liquid phase including the aqueous phase (such as indium nitrate). Alternatively, an indium free crystalline reactant can simply be impregnated with indium source and then calcined at temperatures above 400° C.

The indium free material may have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ $Mg^{++}$, $Ca^{++}$, $Ba^{++}$, $Sr^{++}$, or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

The non-acidic, crystalline, microporous, indium modified material and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

These compositions of the invention exhibit high selectivity for dehydrogenation and/or dehydrocyclization, which is evidenced by the following examples.

Process Significance

Use of the catalyst comprising the indium-modified metal-containing microporous crystalline material in the dehydrocyclization and/or reforming process allows a product of increased aromatic content and of increased octane value over that of the feed. Because of the properties of that catalyst, reforming can be undertaken at low pressures; when light naphtha rich in $C_6$-$C_7$ low octane value hydrocarbons eg., paraffins, are reformed over this catalyst higher net yields of high octane aromatic gasoline are obtained. In one embodiment of this invention, the naphtha is separated into two fractions with the light naphtha processed over the indium containing catalyst while the heavy naphtha can be reformed under conventional reforming conditions.

The post-reforming process of the invention produces a product of increased aromatic content and of increased octane value over that of the feed. More significantly, it allows for increased product liquid yields by eliminating bi-products of hydrocracking.

Integrating conventional reforming of paraffin naphthas with the post reforming process of the invention can result in significant octane gains. Post-processing of reformates from conventional semi-regenerative reformers operating at low octane severity (naphthene and high molecular weight paraffin conversion only) and reaction pressures of 200°-500 psig could result in overall product yields comparable to new low pressure cyclic reforming processes. The process of the invention allows prior operation of the conventional reformer at low octane severity, such that the conversion of $C_6$ and $C_7$ paraffins—the most difficult of the fractions to reform—is minimal and thus could result in lower reforming catalyst aging rates.

EXAMPLES

Example 1

A hydrotreated Arab straight-run (LSR) naphtha was reformed over an indium containing ZSM-5 catalyst comprising 2.3 weight percent platinum, 2.88 weight percent indium, 0.45% sodium and less than 360 ppmw aluminum, with the remaining being silica. The Arab light LSR naphtha used was a $C_6$-210° F. fraction, containing about 42.5% wt $C_6$ paraffins, 32.9% wt $C_7$ parffins, and an RON+O of 51 (calculated). Additional properties and compositional details are described in the following table:

| FEED PROPERTIES ARAB LIGHT LSR NAPHTHA | |
|---|---|
| API Gravity | 73.5 |
| Sulfur, ppmw | 0.06 |
| Nitrogen, ppmw | 0.2 |
| Octane RON + O | 51 |
| Distillation, D-86 | |
| 5% vol., °F. | 157 |
| 50% vol., °F. | 171 |
| 95% vol., °F. | 203 |
| Composition, % wt. | |
| $C_5$ paraffins | 3.3 |
| $C_6$ paraffins | 41.4 |
| $C_6$ naphthenes | 7.4 |
| $C_6$ aromatic | 2.1 |
| $C_7$ paraffins | 32.3 |
| $C_7$ naphthenes | 7.1 |
| $C_7$ aromatic | 3.1 |
| $C_8$ + PNA | 3.3 |

Reforming of the Arab Light LSR naphtha over the platinum-indium ZSM-5 catalyst was conducted at 1000° F., 50 psig, 1.0 LHSV, and 5:1 $H_2$/HC mole ratio at the reactor inlet. These reaction conditions result in 84.9% wt. yield of $C_{5+}$ gasoline at 93.6 RON+O. The $C_{5+}$ gasoline contained 56.8% wt aromatics.

Example 2

Under the same reaction conditions as in Example 1 above, but in the absence of added hydrogen, the RON+O of the $C_5^+$ gasoline increased to 101.8, while the yield remained nearly constant at 84.1% wt. The aromatic content of the $C_{5+}$ gasoline increased to 72.9% wt. It should be noted that no change in performance of the ZSM-5 catalyst was observed in the absence of added hydrogen from 137 to 192 hours on stream at 1000° F., 50 psig and 1.0 LHSV while achieving an average 101 RON+O $C_{5+}$ gasoline in 83.5% wt yield. Data concerning catalyst stability are set forth below:

| Catalyst Stability* | | |
|---|---|---|
| Time on Stream, hours | 136.8 | 192.0 |
| $C_5$ + Gasoline Yield, % wt. | 83.1 | 84.1 |
| $C_5$ + Gasoline Yield, % vol. | 70.6 | 71.6 |
| Octane, RON + O | 100.0 | 101.8 |
| $H_2$ produced, SCF/B | 1980 | 1990 |

*Process Conditions: 1000° F., 50 psig, 1.0 LHSV No added hydrogen

The results of the foregoing examples constitute significant yield and octane advantages when compared with the results expected for processing the LSR naphtha in a conventional semi-regenerative reformer, using a chlorided platinum/alumina catalyst. (See Figure) Typically, conventional reforming of this naphtha would result in about 61% wt yield of 93 RON+O $C_{5+}$ gasoline at reaction conditions of 1000° F., 250 psig, 1.0 LHSV and 10:1 $H_2$/HC mole ratio. The $C_{5+}$ gasoline product contained only 51.2% wt aromatics. Additional details for comparison are set forth in the following Table.

TABLE
REFORMING COMPARISONS

| Catalyst | Pt—Cl/alumina | Pt—In ZSM-5 | |
|---|---|---|---|
| Process Conditions | | | |
| Temperature, °F. | 1000 | 1000 | 1000 |
| Pressure, psig | 250 | 50 | 50 |
| LHSV, 1/hr | 1.0 | 1.0 | 1.0 |
| $H_2$/HC mole ratio | 10 | 5 | — |
| Process Yields, % wt | | | |
| Hydrogen | 0.6 | 3.3 | 4.6 |
| $C_1$-$C_4$ | 38.3 | 11.8 | 11.3 |
| $C_5$ + Gasoline | 61.1 | 84.9 | 84.1 |
| $C_5$ + Product Quality | | | |
| Octane, RON + O | 93.0 | 93.6 | 101.8 |
| Aromatics, % wt | 51.2 | 56.8 | 72.9 |

Reducing the reaction pressure and hydrogen circulation would also improve the selectivity of the conventional reforming catalyst, but would result in unacceptably high aging rates. The ability of the platinum containing indium ZSM-5 catalyst to operate in the absence of added hydrogen appears to offer significant advantages, when compared not only to semi-regenerative, but also cyclic reforming processes using conventional catalysts.

Other compositions to be used in catalytic reforming have been made and are described below.

Example A

Crystalline silicate products were produced containing indium and exhibiting characteristic X-ray diffraction patterns of structures corresponding to ZSM-5, ZSM-11, ZSM-12, ZSM-23, ZSM-48 and ZSM-50.

Table 1A compiles the composition ranges employed in the synthesis of a series of In/ZSM-5 products with widely varying indium content. Also shown in Table 1A is the synthesis of indium-containing silicates having X-ray pattern of ZSM-11, ZSM-12, ZSM-23, ZSM-48 and ZSM-50. The footnotes in Table 1A specify the $SiO_2$ sources and the organic directing agents employed in the synthesis.

TABLE 1A
Crystallizations of Indium-Containing Zeolites 160° C.; Stirred 400 rpm

| Run No. Product | Mixture Composition (Mole Ratios) | | | | | Time, Days | Zeolite |
|---|---|---|---|---|---|---|---|
| | $SiO_2$ / $In_2O_3$ | $H_2O$ / $SiO_2$ | $OH^-$ / $SiO_2$ | $NA^+$ / $SiO_2$ | $R$ / $SiO_2$ | | |
| $1^a$ | 500 | 48 | 0.26 | 0.27 | $0.10^c$ | 3 | ZSM-5 |
| $2^b$ | 500 | 48 | 0.26 | 0.27 | $0.10^c$ | 3 | ZSM-5 |
| $3^a$ | 300 | 48 | 0.26 | 0.28 | $0.10^c$ | 3 | ZSM-5 |
| $4^b$ | 300 | 48 | 0.26 | 0.28 | $0.10^c$ | 1 | ZSM-5 |
| $5^d$ | 300 | 48 | 0.26 | 0.28 | $0.20^b$ | 1 | ZSM-5 |
| $6^b$ | 200 | 48 | 0.26 | 0.30 | $0.10^e$ | 4 | ZSM-48 |
| $7^b$ | 200 | 48 | 0.26 | 0.30 | $0.10^f$ | 4 | ZSM-11 |
| $8^b$ | 150 | 48 | 0.26 | 0.31 | $0.10^c$ | 2 | ZSM-5 |
| $9^b$ | 150 | 48 | 0.26 | 0.31 | $0.10^c$ | 2 | ZSM-5 |
| $10^b$ | 150 | 48 | 0.26 | 0.31 | $0.10^c$ | 2 | ZSM-5 |
| $11^b$ | 150 | 48 | 0.26 | 0.31 | $0.10^c$ | 3 | ZSM-5 |
| $12^b$ | 150 | 48 | 0.26 | 0.31 | $0.10^c$ | 2 | ZSM-5 |
| $13^b$ | 100 | 48 | 0.26 | 0.34 | $0.08^g$ | 3 | ZSM-12 |
| $14^h$ | 76 | 48 | 0.26 | 0.59 | $0.10^c$ | 6 | ZSM-5 |
| $15^i$ | 70 | 40 | 0.20 | 0.23 | $0.10^c$ | 3 | ZSM-5 |
| $16^b$ | 70 | 40 | 0.26 | 0.37 | $0.10^c$ | 3 | ZSM-5 |
| $17^a$ | 60 | 48 | 0.26 | 0.39 | $0.10^c$ | 3 | ZSM-5 |
| $18^b$ | 150 | 40 | 0.20 | 0.25 | $0.10^j$ | 3 | ZSM-23 |
| $19^b$ | 300 | 40 | 0.20 | 0.23 | $0.10^j$ | 3 | ZSM-23 |
| $20^b$ | 300 | 40 | 0.20 | 0.23 | $0.10^k$ | 3 | ZSM-50 |

$^a$Silica source is tetraethylorthosilicate ($Et_4SiO_4$)
$^b$Silica source is SPEX Industries precipitated $SiO_2$
$^c$R = $TPA^+$
$^d$Silica source is DeGussa fumed $SiO_2$
$^e$R = DIQUAT-6 = $(CH_3)_3\overset{+}{N}(CH_2)_6\overset{+}{N}(CH_3)_3$
$^f$R = $TBA^+$
$^g$R = $(CH_3)_2\overset{+}{N}(CH_2)_3\overset{+}{N}(CH_3)_2$
$^h$Q-brand sodium silicate
$^i$Silica source is kieselsaure precipitated $SiO_2$
$^j$R = DIQUAT-7 = $(CH_3)_3\overset{+}{N}(CH_2)_7\overset{+}{N}(CH_3)_3$
$^k$R = Dibenzyldimethylammonium ion Table 2A is a compilation of chemical analyses of some of our indium- containing products. These products vary in indium content from 0.36–5.20 wt % In. The formulas of the zeolite products are expressed in Table 2 as a ratio of oxides per mole of $In_2O_3$.

TABLE 2A
Analyses of Some Indium-Containing Zeolitic Silicate Products

| Sample Run from No. | Weight Percent | | | | | | | Moles C Moles N | Moles per Mole $In_2O_3$ | | | |
|---|---|---|---|---|---|---|---|---|---|---|---|---|
| | C | N | Na | In | $SiO_2$ | $Al_2O_3$ | Ash | | $N_2O$ | $Na_2O$ | $Al_2O_3$ | $SiO_2$ |
| 15 | 6.96 | 0.66 | 3.28 | 5.20 | 62.47 | 0.070 | 85.34 | 12.3 | 1.04 | 3.15 | 0.03 | 46 |
| 14 | 6.74 | 0.43 | 2.64 | 4.19 | 69.94 | 0.24 | 86.20 | 18.3 | 0.84 | 3.14 | 0.13 | 64 |
| 16 | 7.02 | 0.56 | 0.79 | 3.48 | 76.45 | 0.035 | 84.78 | 14.6 | 1.32 | 1.13 | 0.02 | 84 |
| 13 | 6.01 | 0.61 | 0.65 | 2.79 | 81.83 | 0.031 | 91.79 | 11.2 | 1.79 | 1.16 | 0.025 | 112 |
| 9 | 8.02 | 0.71 | 0.98 | 2.11 | 74.85 | 0.078 | 88.05 | 13.6 | 2.36 | 2.29 | 0.06 | 132 |
| 8 | 8.01 | 0.68 | 1.48 | 2.14 | 74.64 | 0.11 | 88.72 | 13.7 | 2.61 | 3.45 | 0.11 | 133 |
| 12 | 7.93 | 0.74 | 0.56 | 2.26 | 83.85 | 0.005 | 88.05 | 12.4 | 2.68 | 1.23 | 0.009 | 142 |
| 10 | 8.37 | 0.81 | 1.83 | 1.92 | 73.14 | 0.025 | 88.36 | 12.0 | 3.46 | 4.76 | 0.03 | 146 |
| 11 | 8.22 | 0.62 | 0.54 | 1.49 | 82.14 | 0.031 | 85.96 | 15.5 | 3.41 | 1.81 | 0.05 | 211 |
| 6 | 4.58 | 0.79 | 0.48 | 1.46 | 86.70 | 0.029 | 91.86 | 6.7 | 4.44 | 1.64 | 0.045 | 227 |
| 7 | 8.66 | 0.51 | 0.44 | 0.96 | 82.29 | 0.013 | 89.43 | 19.8 | 4.36 | 2.29 | 0.045 | 328 |
| 2 | 8.12 | 0.69 | 0.40 | 0.36 | 78.05 | 0.083 | 85.69 | 13.7 | 15.7 | 5.55 | 0.52 | 830 |

Example B

The In/ZSM-5 of that run No. 12 was prepared as follows:

The source of the indium can be incorporated into the zeolitic silicate synthesis reaction mixture as a partial, or preferably as a complete substitute for sources of alumina (or boron) conventially used in zeolite synthesis. In the embodiments described below the crystalline indium containing silicates were synthesized from crystallization reaction mixtures which contained no deliberately added sources of Al₂O₃.

A commercial silica gel (SPEX Ind.) with very low aluminum contamination was employed in the synthesis of In-ZSM-5. First, 0.85 g In(NO₃)₃ and 2.66 g NaOH pellets were dissolved in 180.2 g de-ionized water, then 5.64 g tetrapropylammonium bromide (TPABr) was dissolved in this basic solution. This solution was transferred to a 300 ml stainless steel autoclave, and 15.0 g of silica gel (SPEX) was added. The autoclave was then sealed and stirring and heating was begun. The hydrogel formed by this reaction mixture is described by the following mole ratios:

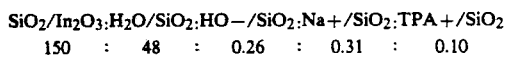

| 150 : 48 : 0.26 : 0.31 : 0.10 |

The hydrogel was reacted at 1600° C. for 2 days at a stirring rate of 400 rpm before quenching. The resultant crystalline product was filtered, washed, and dried. X-ray powder diffraction analysis showed the product to be 100% crystalline ZSM-5, when compared to the diffraction pattern of a conventional ZSM-5. Elemental analysis of the ZSM-5 product gave: C=7.93 wgt %, N=0.74%, Na=0.56%, In=2.26%, Al 0.005%, SiO₂=83.85%, Ash=88.05%.

These results expressed in mole ratios were: C/N=12.5; Moles/mole In₂O₃: N₂O=2.68, Na₂O=1.23, Al₂O₃=0.009, SiO₂=142.

Platinum incorporation was undertaken as follows: The as-synthesized zeolite was heated in nitrogen to 520° C. at 1 C/min and held there for 6 hour. It was then calcined in air in a similar manner. The calcined zeolite analyzed for 41.05% Si, 2.21% In (Si/In2=152), and 120 ppm Al, and sorbed 10.4% n-hexane at 90° C. The calcined zeolite (3 g) was stirred in a solution of 150 mg Pt(NH₃)₄Cl₂ in 100 ml water at room temperature overnight. After being washed, filtered and dried, the ion-exchanged zeolite was found to contain 0.41 meq NH₃/g ash, which is equivalent to 1.89% Pt on sample. The platinum tetramine zeolite was then calcined in oxygen to 350° C. at 0.5 C/min and held there for 1 hour. Elemental analysis indicated the presence of 1.85% Pt on the final catalyst.

A standard test (based on hexane conversion at 1000° F.) indicated a hexane conversion activity between 200 and 500, with a very high benzene selectivity (60%). At very high hexane conversions (99%), benzene was formed in over 94% yield. Similarly, n-heptane yielded 96% toluene. Similarly, n-heptane yielded 96% toluene. Consistent with the non-acidic nature of this platinum catalyst, n-octane yielded predominantly ethylbenzene and ortho-xylene, 2-methylheptane produced mostly meta-xylene, and 3-methylheptane formed mainly ethylbenzene, para-, and ortho-xylene.

Example C

In Example A, zeolitic silicate was made using In(NO₃)₃ in the crystallization reaction mixture. In this example indium was incorporated post-synthesis; in a subsequent step platinum was ion-exchanged onto the zeolite.

In this example, a high silica/alumina (10,000) ZSM-11 was calcined in nitrogen and then in air at 538° C. InCl₃ vapors were passed through the zeolite in a stream of nitrogen, while it was heated to 500° C. at 10 C/min. The zeolite was maintained at 500° C. for 1.5 hours. After cooling, the catalyst was added to 200 ml 1M NH₄Cl adjusted to pH 9.5 with NH₄OH. The mixture was stirred for 20 minutes at room temperature, and then filtered. The zeolite was then reexchanged for 3 hours with 1M NH₄Cl adjusted to pH 7.6. Thermogravimetric analysis indicated the presence of 0.325 meq/g ammonium ion in the zeolite.

Platinum was incorporated by ion exchange with Pt(NH₃)₄Cl₂ at room temperature. The platinum zeolite was then calcined in oxygen to 350° C. at 0.5° C./min.

The "non-acidic" nature of the catalyst was confirmed by its ability to aromatize n-heptane to toluene in high yield. At about 500° C. (up to about 538° C.) and 30 torr heptane in nitrogen, toluene was formed in 94% selectivity at a conversion level of greater than 90%.

Example D

The ZSM-5-type borosilicate was synthesized at 170° C. from a mixture of 12.4 g high purity silica (SPEX), 105 g 20% TEA hydroxide, and 0.8 g boric acid. The as-synthesized zeolite was then calcined in nitrogen and then in air at 520° C. The calcined zeolite contained 41.39% Si, 0.015% Al, and 0.41% B.

Two grams of the calcined borosilicate was impregnated with 135 mg In(NO₃)₃, and calcined in air at 500° C. for 2 hours. 1.8 g of this material was then ion-exchanged with 28 mg Pt(NH₃)₄Cl₂ in 100 ml water at room temperature. TGA analysis in hydrogen indicated the presence of 0.18 meq N/g equivalent to 0.87% Pt. The platinum-exchanged zeolite was then calcined in oxygen to 350° C. at 0.5° C./min.

The catalyst activity of the foregoing composition was examined. The "non-acidic" nature of the catalyst was confirmed by its ability to aromatize n-heptane to toluene in high yield. At 500° C. and 30 torr heptane in nitrogen, toluene was formed in 95% yield. Furthermore, the small amounts of both methane and propane produced were exceeded by the ethane formed, indicative of the low hydrogenolysis and acid activity of the catalyst.

| % Conversion | % C1 | % C2 | % Benzene | % Toluene (Selectivity) |
|---|---|---|---|---|
| 96 | 0.4 | 0.6 | 1.3 | 92 (96%) |
| 99 | 0.5 | 1.0 | 1.5 | 95 (96%) |

Table 2A is a compilation of chemical analyses of some of our indium-containing zeolitic products. These products vary in indium content from 0.36–5.20 wt % In. The formulas of the zeolite products are expressed in Table 2 as a ratio of oxides per mole of In₂O₃.

Example E

Indium-containing zeolite ZSM-20 was synthesized by the following procedure:

12.75 grams of sodium aluminate (NaAlO₂) and 6.02 grams indium nitrate were dissolved in 57.96 grams of deionized water. After the solid ingredients dissolved, 484.1 ml of 2.88 N tetraethylammonium hydroxide (TEAOH) was added to the solution. The resulting solution was not styirred intyo 312.5 grams of tetraethylorthosilicate. This solution was kept stirring for one hour until the hydrolysis reaction was complete. The resulting hydrogel was now transferred to a one-liter polypropylene bottle.

The polypropylene bottle was loosely capped and placed into a steambox (100° C.) to promote the crystallization of the zeolite. The next morning the bottle was removed from the steambox and the bottle cap was now closed tightly. The bottle was shaken vigorously, then replaced into the steambox. The reaction mixture for the initial hydrogel formed for the synthesis of the indium-containing ZSM-20 can be described by the following set of mole ratios:

| | |
|---|---|
| $SiO_2/In_2O_3$ | 150 |
| $H_2O/SiO_2$ | 10 |
| $OH^-/SiO_2$ | 0.9 |
| $Na^+/SiO_2$ | 0.09 |
| $TEA^+/SiO_2$ | 0.93 |
| $SiO_2/Al_2O_3$ | 30 |

Samples of the solid product were removed daily from the polypropylene bottle for X-ray diffraction (XRD) analysis to determine the product crystallinity. XRD analysis showed that the ZSM-20 crystallization was complete in 14 days. The polypropylene bottle was removed from the steambox, and the solid product was filtered on a Büchner funnel. After filtration, the product zeolite was boiled in de-ionized water and again filtered and dried under an infrared heat lamp. After drying, a sample of the product was submitted for XRD and chemical analysis. XRD analysis showed the product to be zeolite ZSM-20. The chemical analysis for the indium-containing ZSM-20 was:

| Weight Percent | | | | | | |
|---|---|---|---|---|---|---|
| C | N | Na | In | $SiO_2$ | $Al_2O_3$ | Ash |
| 10.0 | 1.2 | 3.0 | 3.08 | 58.5 | 11.4 | 75.1 | which gives:

| Moles C | Moles per Mole $In_2O_3$ | | | |
|---|---|---|---|---|
| Moles N | $N_2O$ : | $Na_2O$ : | $Al_2O_3$ : | $SiO_2$ |
| 9.7 | 3.19 | 4.86 | 8.33 | 72.7 |

Example F

Indium-containing zeolite Beta was synthesized in the following manner:

95 grams of sodium aluminate and 4.68 grams of indium nitrate were dissolved in 85.14 grams of de-ionized water. After the salts dissolved, 105.0 ml of 3.1 N TEAOH was added to the solution. The resulting solution was transferred to a 300 ml stainless-steel autoclave.

Now 46.67 grams of solid silica gel (SPEX Industries) was poured into the autoclave, the autoclave was sealed and stirring and heating begun immediately. The reaction was carried out at 160° C. with stirring (400 rpm).

The initial reaction mixture for the synthesis of indium-containing zeolite Beta can be described by the mole ratios:

| | |
|---|---|
| $SiO_2/In_2O_3$ | 90 |
| $H_2O/SiO_2$ | 12 |
| $OH^-/SiO_2$ | 0.40 |
| $Na^+/SiO_2$ | 0.09 |
| $TEA^+/SiO_2$ | 0.46 |
| $SiO_2/Al_2O_3$ | 30 |

After 4 days the autoclave was quenched in a water plus ice bath to terminate the reaction. The solid product was filtered, boiled in water and again filtered. XRD analysis showed the crystalline product to be zeolite Beta. Chemical analysis of the indium-containing zeolite Beta product gave the following results:

| Weight Percent | | | | | | |
|---|---|---|---|---|---|---|
| C | N | Na | In | $SiO_2$ | $Al_2O_3$ | Ash |
| 10.84 | 1.71 | 1.4 | 2.5 | 69.8 | 4.2 | 79.92 | which gives

| Moles C | Moles per Mole $In_2O_3$ | | | |
|---|---|---|---|---|
| Moles N | $N_2O$ : | $Na_2O$ : | $Al_2O_3$ : | $SiO_2$ |
| 7.4 | 5.61 | 2.79 | 3.78 | 62.8 |

Example G

Indium-containing crystalline aluminophosphate molecular sieve ALPO-5 was synthesized as follows:

23.1 grams of concentrated phosphoric acid (86.3% $H_3PO_4$) was diluted with 30.0 grams of de-ionized water. Now 10.0 grams of Kaiser alumina was stirred into this acid solution and the mixture was digested for 45 minutes at 90° C. with continuous stirring. After the digestion period a solution containing 1.18 grams of indium nitrate dissolved in 41.0 grams of de-ionized water was stirred into the gel. Finally, 37.0 grams of 40% wt. TEAOH solution was stirred into the gel and stirring continued until a uniform gel was produced. This gel was not transferred to a 300 ml stainless-steel autoclave. The resulting reaction mixture hydrogel can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $TEA^+/Al_2O_3$ | 1.0 |

The autoclave was sealed and heated and stirring began immediately. The reaction was carried out at 160° C. with stirring (400 rpm).

After 4 days the autoclave was quenched in a water+ice bath to terminate the crystallization. The solid product was filtered, boiled in water and filtered again. After drying the product, XRD analysis showed the material to be crystalline aluminophosphate designated by Union Carbide as ALPO-5. Chemical analysis of the indium-containing ALPO-5 gave:

| Weight Percent | | | | | | |
|---|---|---|---|---|---|---|
| C | N | Na | P | Al | In | Ash |
| 6.66 | 0.84 | 0.48 | 21.05 | 16.01 | 1.44 | 89.45 | which gives:

| Moles C | Moles per Mole $In_2O_3$ | | | |
|---|---|---|---|---|
| Moles N | $N_2O$ : | $Na_2$ : | $P_2O_5$ : | $Al_2O_3$ |
| 9.2 | 4.78 | 1.66 | 54.2 | 47.3 |

Example H

Indium-containing crystalline silicoaluminophosphate molecular sieve SAPO-5 was synthesized in a manner analogous to Example G:

46.2 grams of concentrated phosphoric acid (86.3% $H_3PO_4$) was first diluted with 60.0 grams of de-ionized water then 20.0 grams of Kaiser alumina was added to the solution. This mixture was now digested on a hot plate at 90° C. for 45 minutes, with continuous sitrring. At the end of the digestion period, a solution containing 2.36 grams of indium nitrate dissolved in 82.0 grams of de-ionized water was stirred into the gel. Next 74.0 grams of 40% wt TEAOH solution was sitrred into the gel. This mixture was now stirred at room temperature until a uniform hydrogel was produced. The resulting hydrogel was transferred to a one-liter stainless-steel autoclave. Before sealing the autoclave, 2.04 grams of tetraethylorthosilicate was transferred to the autoclave. The autoclave was then sealed and heating and stirring was begun immediately. The resulting reaction mixture can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $SiO_2/Al_2O_3$ | 0.10 |
| $TEA^+/Al_2O_3$ | 1.0 |

The crystallization of the indium-containing SAPO was carried out at 150° C. with stirring (400 rpm).

At the end of 4 days the autoclave was quenched in a water+ice bath to terminate the crystallization. The solid product was filtered, boiled in water, and re-filtered. After drying under a heat lamp, XRD analysis showed that the reflection lines for the product corresponded to silicoaluminophosphate SAPO-5, a Union Carbide designation for this material.

Chemical analysis of the indium-containing SAPO-5 gave:

| Weight Percent | | | | | | | |
|---|---|---|---|---|---|---|---|
| C | N | Na | P | Al | In | Si | Ash |
| 6.32 | 0.60 | 0.48 | 19.88 | 15.71 | 1.45 | 0.66 | 85.00 | which gave

| Moles C | | Moles per Mole $In_2O_3$ | | | | | | |
|---|---|---|---|---|---|---|---|---|
| Moles N | $N_2O$ | : | $Na_2O$ | : | $P_2O_5$ | : | $Al_2O_3$ | : | $SiO_2$ |
| 12.3 | 3.39 | | 1.65 | | 50.8 | | 46.1 | | 3.7 |

Example I

Platinum incorporation into the indium-containing silicate of ZSM-5 structure was carried out by direct addition of a platinum compound to the zeolite synthesis reaction mixture as follows:

A solution was prepared by dissolving 2.00 grams of indium nitrate and 13.07 grams of NaOH pellets in 710.28 grams of de-ionized water. After the solids dissolved, 26.6 grams of tetrapropylammonium bromide (TPABr) was dissolved in the solution. Finally 1.29 grams of platinum tetraaminenitrate [$Pt(NH_3)_4(NO_3)_2$] was dissolved in the solution, and the solution was transferred to a one-liter stainless-steel autoclave. Before sealing the autoclave, 66.67 grams of commercial silica gel (SPEX Industries) was poured into the autoclave. The autoclave was then sealed and heating and stirring was begun immediately. The reaction mixture hydrogel can be described by the following mole ratios:

| | |
|---|---|
| $SiO_2/In_2O_3$ | 300 |
| $H_2O/SiO_2$ | 40 |
| $OH^-/SiO_2$ | 0.30 |
| $Na^+/SiO_2$ | 0.33 |
| $TPA^+/SiO_2$ | 0.10 |
| $SiO_2/Pt$ | 300 |

The crystallization was carried out at 170° C. with stirring (400 rpm).

After 4 days the autoclave was quenched in a water-+ice bath to terminate the crystallization. In the usual manner the solid product was filtered, boiled in water, and finally filtered again before drying under a heat lamp. XRD analysis of the solid product showed the material to be crystalline zeolite ZSM-5.

Chemical analysis of the indium-containing ZSM-5 product gave:

| Weight Percent | | | | | | | |
|---|---|---|---|---|---|---|---|
| C | N | Na | In | Pt | $SiO_2$ | $Al_2O_3$ | Ash |
| 8.27 | 0.74 | 1.3 | 1.1 | 0.52 | 82.7 | 0.0265 | 85.05 | which gave:

| Moles C | | Moles per Mole $In_2O_3$ | | | | | | |
|---|---|---|---|---|---|---|---|---|
| Moles N | $N_2O$ | : | $Na_2O$ | : | $Al_2O_3$ | : | $SiO_2$ | : | Pt |
| 13.1 | 5.52 | | 5.90 | | 0.05 | | 288 | | 0.55 |

Example J

A boron-containing zeolite beta was synthesized and then calcined to remove the organic template, by heating first in $N_2$ 25°–530° at 10/min and held 6 hrs. then in air in $N_2$ 25°–530° at 10/min. and held 6 hours.

25 g of the calcined zeolite was ion-exchanged with 750 mg $Pt(NH_3)_4$ $Cl_2$ in 100 ml $H_2O$ at room temperature overnight. The dried material was then calcined in flowing oxygen (100 cc/min.) 25°–350° at ½° /min. and held 1 hour.

10 g of the calcined Pt-containing zeolite was then treated with 0.9 g $In(NO_3)_3$ $H_2O$ in 200 ml $H_2O$ at room temperature overnight.

The zeolite was filtered and washed.

The In-containing Pt/zeolite was added to 150 ml $H_2O$ and titrated to pH 9.0 with 0.5 M CsOH (1½ hrs). The material was filtered, washed, and dried. The final product contained 0.76% Pt, 11% Cs, 1.1% In, and 0.08% B.

EXAMPLE K

The synthesis of a binary oxide zeolite having the structure of ZSM-5 was carried out in the two-phase system as in Ser. No. 878,555 filed June 26, 1986. The aqueous phase of the two-phase system comprised 2.8 g $In(NO_3)_3xH_2O$ dissolved in 35 g water to which was added 63 g TPAOH (40% in $H_2O$). Constituting the organic phase was 77.0 g $Si(OCH_3)_4$ dissolved in 35 g of 1-hexanol. The mixture was nucleated at 180° C. for 24 hours and crystallized at 200° C. for 144 hours. The final product was filtered and washed. The X-ray diffraction pattern of the dried material proved it to be well-crystallized ZSM-5.

The sample was ammonium-exchanged (1M NH$_4$Cl, twice, 60° C., 20 ml/g zeolite) and calcined. The chemical composition of the ash of a 1000° C. calcined sample was 79.3 wt. % SiO$_2$ and 1.5 wt. % In$_2$O$_3$. The ash residue also contained a small quantity, i.e. 85 ppm, of aluminum.

Temperature-programmed desorption of ammonia indicated an exchange capacity of 0.09 meq/g for the product of this example. The Si/In ratio from TPAD was 190.5. The sample had an Alpha Value of 1.0.

The particle size of the product from this example was about 0.2 microns. The particles were made of pure single crystals with almost cubic appearance.

EXAMPLE L

The synthesis of Example K was repeated, except that the mixture contained 3.6 g In(NO$_3$)$_3$xH$_2$O in the aqueous phase. The product material was filtered and dried. It had the same characteristic ZSM-5 X-ray lines as the product of Example K. The material was calcined and ammonium-exchanged as described in Example K. The chemical composition of the ash of a 1000° C. calcined sample was 78.2 wt. % SiO$_2$ and 3.1 wt. % In$_2$O$_3$. The ash residue also contained a small quantity, i.e. 180 ppm, of aluminum.

Temperature-programmed desorption of ammonia indicated an exchange capacity of 0.21 meq/g for the product of this example. The Si/In ratio from TPAD was 77.9. The sample had an Alpha Value of 2.5.

The particle size of the product from this example was about 0.2 microns. The particles were made of crystals with almost cubic appearance. There were no impurities present.

EXAMPLES M-Q

The synthesis of Example K was repeated, except that the mixtures contained varying amounts of In(NO$_3$)$_3$xH$_2$O. Five preparations were made, with the following compositions:

|  | Example | | | | |
|---|---|---|---|---|---|
|  | M | N | O | P | Q |
| Aqueous Phase (g) | | | | | |
| H$_2$O | 40.0 | 40.0 | 35.0 | 40.0 | 40.0 |
| In(NO$_3$)$_3$ × H$_2$O | 0.9 | 7.2 | 1.8 | 1.8 | 3.6 |
| TPAOH, 40% | 63.0 | 63.0 | 63.0 | 63.0 | 63.0 |
| Organic Phase (g) | | | | | |
| 1-Hexanol | 60.0 | 60.0 | 35.0 | 60.0 | 60.0 |
| Si(OCH$_3$)$_4$ | 77.0 | 77.0 | 77.0 | 77.0 | 77.0 |

The product materials were filtered and dried. They had the same characteristic X-ray lines as ZSM-5. The materials were calcined and ammonium-exchanged as in Example K. Their properties were as follows:

|  | Example | | | | |
|---|---|---|---|---|---|
|  | M | N | O | P | Q |
| SiO$_2$, wt. % | 84.0 | 77.5 | 80.5 | 76.7 | 82.5 |
| In$_2$O$_3$, wt. % | 0.67 | 5.1 | 1.58 | 1.31 | 2.92 |
| Al, ppm | 105 | 65 | 130 | 85 | 60 |
| Exchange Capacity, meq/g | 0.09 | 0.17 | 0.17 | 0.12 | 0.21 |
| Si/In (from TPAD) | 193 | 99 | 95 | 138 | 77 |
| Alpha Value | 1.5 | 1.6 | 1.0 | 1.0 | n.d. |
| Particle size | 2000A | 1 micr | 2000A | 2000A | 2000A |

EXAMPLE 3

The reforming experiments herein were undertaken by reforming a hydrotreated Arab Light LSR (light straight-run) over a platinum containing indium ZSM-5 catalyst at 1000° F., 50 psig, 1.0 LHSV while varying hydrogen pressure at the reactor inlet. The Arab light LSR naphtha used was a C$_6$-201° F. fraction, containing about 42.5% wt C$_6$ paraffins, 32.9% wt C$_7$ paraffins, and an RON+O of 51 (calculated). Additional properties and compositional details are described in the following table:

| FEED PROPERTIES ARAB LIGHT LSR NAPHTHA | |
|---|---|
| API Gravity | 73.5 |
| Sulfur, ppmw | 0.06 |
| Nitrogen, ppmw | 0.2 |
| Octane RON + O (calculated) | 51 |
| Distillation, D-86 | |
| 5% vol., °F. | 157 |
| 50% vol., °F. | 171 |
| 95% vol., °F. | 203 |
| Composition, % wt. | |
| C$_5$ paraffins | 3.3 |
| C$_6$ paraffins | 41.4 |
| C$_6$ naphthenes | 7.4 |
| C$_6$ aromatic | 2.1 |
| C$_7$ paraffins | 32.3 |
| C$_7$ naphthenes | 7.1 |
| C$_7$ aromatic | 3.1 |
| C$_8$+ PNA | 3.3 |

The catalyst contains 2.3 weight % platinum; 2.88 weight percent indium, 0.45% sodium, and less than 360 ppmw aluminum with the remainder being silica.

The results show that reducing the hydrogen partial pressure in the reactor significantly improves the activity and selectivity of the catalyst.

| REFORMING LSR NAPHTHA EFFECT OF REDUCING HYDROGEN PRESSURE | | | |
|---|---|---|---|
|  | Inlet Gas/HC Feed mole ratio | | |
|  | 5:1 H$_2$/HC | NO ADDED H$_2$ | 5:1 He/HC |
| Hydrogen, % wt. | 3.3 | 4.6 | 5.7 |
| C1-C4 | 11.8 | 11.3 | 3.8 |
| C5+ Gasoline | 84.9 | 84.1 | 90.5 |
| C5+ RON + O | 93.6 | 101.8 | 103.3 |
| Aromatics, % wt. | 48.0 | 61.0 | 68.7 |

Eliminating any added hydrogen at the reactor inlet increases the aromatics selectivity and results in a substantial gain in octane while maintaining gasoline yield. Introducing an inert carrier, in this example helium, to further reduce the partial pressure of hydrogen in the reactor results in additional yield and octane gains by further improving aromatics selectivity. Hydrogenolysis and cracking reactions which result in C$_1$-C$_4$ make are suppressed. Both hydrogen yield and purity increase as a result.

EXAMPLE 4

In this example the pretreated light paraffinic naphtha used in Example 3 was processed over a silica-bound Pt/[In]ZSM-5 catalyst while cofeeding hydrogen and propane. A second experiment using hydrogen only as a cofeed with the naphtha is shown for comparison. Reaction conditions were 1000° F., 50 psig and 1.0 LHSV on naphtha feed, with 12:1 hydrogen or hydrogen+propane to naphtha mole ratio at the reactor inlet. The naphtha partial pressure (4 psi) was therefor the same in both experiments, while the hydrogen partial pressure was lowered from 46 psi to 12 psi by cofeeding propane as the diluent.

| LOW PRESSURE REFORMING WITH PROPANE COFEED | | | |
|---|---|---|---|
| | Feed | $H_2$ Only | $H_2 + C_3$ |
| $H_2/C_5+$ HC Mole Ratio | — | 12:1 | 3:1 |
| $C_3/C_5+$ HC Mole Ratio | — | — | 9:1 |
| $C_3$ vol. % on naphtha | 577.0 | 11.1 | 546.0 |
| $C_3-$ Yield, vol. % | — | 0.7 | 33.0 |
| $C_5+$ Gasoline Yield, vol. % | 100.0 | 75.3 | 81.0 |
| $C_5+$ Gasoline Octane RUN + O | 51 | 83 | 91 |
| Hydrogen Produced, SCF/B | — | 580 | 1954 |
| Hydrogen Purity, mole % | — | 79.0 | 96.9 |
| Aromatics, wt. % | 5.2 | 29.4 | 44.9 |

Cofeeding propane to reduce the hydrogen partial pressure improves aromatization selectivity and results in both increased gasoline yield and higher (calculated) octane. Dehydrogenation of the propane cofeed to propylene and hydrogen approaches thermodynamic equilibrium at the reaction conditions chosen. There is a significant increase in the hydrogen purity (defined as moles hydrogen relative to total moles hydrogen, methane and ethane), and the quantity of hydrogen produced. Note that the propane diluent and higher hydrocarbons are easily separated from the hydrogen produced, thereby ensuring economical recovery of the high purity hydrogen.

The catalyst used in this experiment was prepared by extruding an as-synthesized TPANa [In]ZSM-5 50/50 with silica according to the method of Bowes (U.S. Pat. No. 4,582,815). The extrudate was calcined in nitrogen and then air at 538° C. and then ion-exchanged with platinum tetrammine chloride solution, which was then calcined in oxygen from 25° to 350° C. at ½ C/min and held at 350° C. for 1 hour. The calcined catalyst which resulted contained 0.48 wt. % platinum, 0.49 wt. % indium, 0.11 wt. % aluminum, and 0.12 wt. % sodium.

Example 5

Post-processing of a reformate of about 70 RON+O over a platinum indium silicate having an x-ray diffraction pattern of ZSM-5 was undertaken.

The reformate used as feed was obtained by sampling the second reactor of a three reactor reforming process in which the reforming catalyst was a conventional chlorided platinum catalyst. The paraffins which would have been converted in the third reactor remained, resulting in the relatively low octane number. This reformate was characterized by a research octane number of 67.7, a combined hydrogen content of 13.75%, and contained 2.7% wt. $C_5$ paraffins, 52.4% wt. $C_{6+}$ paraffins, 10.6% wt. naphthenes, and 33.7% wt. aromatics.

The platinum containing indium ZSM-5 catalyst used in the experiments contained 2.3 weight % platinum; 2.88 weight percent indium, 0.45% sodium and less than 360 ppmw aluminum with the remainder being silica. The catalyst had been used for approximately 18 days in reforming light straight-run (LSR) Arab Light Naphtha prior to the post-reforming experiments.

The following comparison shows the results observed when post-processing low octane reformate at 1000 F., 50 psig and 1.0 LHSV, with either hydrogen or helium at the inlet.

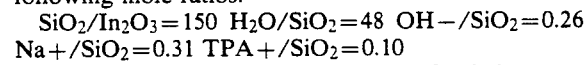

| | FEED | 5:1 $H_2$/HC | 5:1 He/HC |
|---|---|---|---|
| Hydrogen, % wt. | — | −0.2 | 1.6 |
| C1-C4 | — | 15.5 | 1.9 |
| C5+ Gasoline | 100.0 | 84.5 | 96.5 |
| C5+ RON + O | 67.7 | 89.0 | 93.2 |
| C5+ Aromatics, % wt. | 34.6 | 43.9 | 57.4 |

From the results above, it is noted that post-processing of the low octane paraffinic reformate over the platinum containing indium ZSM-5 catalyst clearly improves the gasoline octane. Reducing the hydrogen partial pressure in the reactor by cofeeding a diluent stream improves the aromatics selectivity, and results in both higher gasoline yield and octane.

Example 6

This example illustrates the preparation of a non-acidic indium-containing ZSM-5. (The preparation and catalyst are not per se part of the present invention).

A commercial silica gel (SPEX Ind.) with very low aluminum contamination was employed in the synthesis of In-ZSM-5. First, 0.85 g $In(NO_3)_3$ and 2.66 g NaOH pellets were dissolved in 180.2 g de-ionized water, then 5.64 g tetrapropylammonium bromide (TPABr) was dissolved in this basic solution. This solution was transferred to a 300 ml stainless steel autoclave, and 15.0 g of silica gel (SPEX) was added. The autoclave was then sealed and stirring and heating was begun. The hydrogel formed by this reaction mixture is described by the following mole ratios:

$SiO_2/In_2O_3 = 150$  $H_2O/SiO_2 = 48$  $OH-/SiO_2 = 0.26$
$Na+/SiO_2 = 0.31$  $TPA+/SiO_2 = 0.10$

The hydrogel was reacted at 160 C. for 2 days at a stirring rate of 400 rpm before quenching. The resultant crystalline product was filtered, washed, and dried. X-ray powder diffraction analysis showed the product to be 100% crystalline ZSM-, when compared to the diffraction pattern of a conventional ZSM-5. Elemental analysis of the ZSM-5 product gave: C=7.93 wt %, N=0.56%, In=2.26%, Al=0.005%, $SiO_2$=83.85%, Ash=88.05%.

Platinum incorporation was undertaken as follows: The as-synthesized zeolite was heated in nitrogen to 520° C. at 1° C./min. and held there for 6 hours. It was then calcined in air in a similar manner. The calcined zeolite analyzed for 41.05% Si, 2.21% In (Si/In2=152), and 120 ppm Al, and sorbed 10.4% n-hexane at 90° C. The calcined zeolite (3 g) was stirred in a solution of 150 mg $Pt(NH_3)_4Cl_2$ in 100 ml water at room temperature overnight. After being washed, filtered, and dried, the ion-exchanged zeolite was found to contain 0.41 meq $NH_3$/g ash, which is equivalent to 1.89% Pt on sample. The platinum tetramine zeolite was then calcined in oxygen to 350° C. at 0.5° C./min and held there for 1 hour. Elemental analysis indicated the presence of 1.85% Pt on the final catalyst.

Example 7

Normal hexane was contacted with the indium-containing catalyst of Example 6 under conditions similar to those shown in Example 2. At very high conversions (99%), benzene was formed in over 94% yield. Similarly, normal heptane yielded 96% toluene.

What is claimed is:

1. A process for manufacturing benzene, toluene, or mixtures thereof, said process comprising providing a feed comprising substantially isomer-free normal hexane, substantially isomer-free normal heptane, or mixtures thereof and contacting said feed under dehydrocyclization conditions of temperature, pressure and space velocity with a non-acidic dehydrogenation catalyst consisting essentially of a platinum group metal supported on an indium containing zeolite, said zeolite having the crystal structure of ZSM-5, ZSM-11, ZSM-12, ZSM-23, ZSM-35, ZSM-38 or ZSM-48, and recovering said benzene, toluene or mixture thereof.

2. The process described in claim 1 wherein said conversion conditions include a temperature of about 400° C. to about 600° C., a pressure of 5 to about 500 psi (absolute) and a hexane and/or heptane WHSV of 0.1 to 10.0, and wherein said catalyst comprises 0.1 to 20 wt % of platinum group metal and 0.05 to 20 wt % of indium.

3. The process of claim 2 wherein said zeolite contains less than about 0.1 wt % alumina.

4. The process of claim 1 wherein said feed contains one or more diluents selected from the group consisting of hydrogen gas, an inert gas, and an aliphatic hydrocarbon having one to five carbon atoms.

5. The process of claim 2 wherein said feed contains one or more diluents selected from the group consisting of hydrogen gas, an inert gas, and an aliphatic hydrocarbon having one to five carbon atoms.

6. The process of claim 1 wherein said zeolite has the crystal structure of ZSM-5 and said dehydrogenation metal is platinum.

7. The process of claim 2 wherein said zeolite has the crystal structure of ZSM-5 and said dehydrogenation metal is platinum.

8. The process of claim 5 wherein said zeolite has the crystal structure of ZSM-5 and said dehydrogenation metal is platinum.

9. A process for manufacturing benzene or toluene or mixtures thereof, said process comprising, in combination:

fractionally distilling a straight-run paraffinic gasoline and recovering a fraction rich in normal hexane or normal heptane or a mixture thereof;

contacting said recovered fraction with a Type 5A molecular sieve whereby sorbing said normal paraffin or paraffins from said recovered fraction and recovering a substantially isomer-free normal paraffin or paraffins;

and contacting under dehydrogenation conditions said substantially isomer-free normal paraffin or paraffins with a non-acidc dehydrogenation catalyst consisting essentially of a platinum group metal supported on an indium containing zeolite, said zeolite having the crystal strucutre of ZSm-5, ZSM-11, ZSM-12, ZSM-23, ZSM-35, ZSM-38 or ZSM-48.

10. A process for reforming a naphtha feedstock of low octane value comprising contacting the feedstock, under reforming conditions, with a catalyst composition consisting of a reforming hydrogenation/dehydrogenation metal in combination with a non-acidic microporous crystalline material containing indium which exhibits the X-ray diffraction of ZSM-5, ZSM-11, ZSM-12, ZSM-20, ZSM-23, ZSM-48, ZSM 50, and recovering a reformate having an octane value greater than that of the feedstock and having an aromatic content greater than that of the feed.

11. The process of claim 10, wherein said reforming metal comprises 0.1 to 20 weight percent of the catalyst and said indium comprises 0.05 to 20 weight percent of the combination.

12. The process of claim 10, wherein said reforming conditions further includes adding hydrogen to the feedstock.

13. The process of claim 10, wherein the naphtha feedstock comprises a light naphtha fraction of $C_6$ to 250° F. boiling range components.

14. The process of claim 10, wherein the naphtha feedstock is separated into at least two fractions including a fraction containing $C_6$-$C_7$ paraffins wherein said fraction containing $C_6$-$C_7$ paraffins is contacted with said catalyst.

15. The process of claim 14, wherein a second fraction of said two fractions is subjected to reforming conditions including pressures of about 0 to 500 psig, temperatures of 800° to 1100° F.; $H_2$/HC molar ratios of 1 to 20:1 LHSV of 0.1 to 20 $hr^{-1}$.

16. The process of claim 10, wherein the zeolite is ZSM-5.

17. The process of claim 10, wherein the aluminum content of the non-acidic crystalline microporous material is less than 0.1 weight percent.

18. The process of claim 10, wherein the aluminum content of the non-acidic microporous crystalline material is less than 0.02 weight percent.

19. The process of claim 10, wherein the reforming metal is a Group VIII metal.

20. The process of claim 10, wherein the hydrogenation/dehydrogenation metal is a platinum group metal.

21. The process of claim 10, wherein the hydrogenation/dehydrogenation metal is platinum.

22. The process of claim 10, wherein the pressure of the reforming conditions ranges from 0 to 500 psig.

23. The process of claim 14, wherein the pressure of reforming ranges from 0 to 500 psig.

24. The process of claim 10, wherein the liquid yield exceeds the liquid yield of reforming undertaken in the presence of the indium free counterpart of the non-acidic crystalline microporous material.

25. The process of claim 14, wherein the liquid yield exceeds the liquid yield of reforming undertaken in the presence of the indium free counterpart of the non-acidic crystalline microporous material.

26. The process of claim 11, wherein the temperature of reforming ranges from 800° to 1100° F.

27. The process of claim 10, wherein the feedstock, prior to said contacting, is subjected to fractionation to remove the fraction boiling below about 150° F.

28. A process for upgrading a naphtha comprising in combination:

providing a feedstream which is a paraffin rich naphtha;

contacting the feedstream with a catalyst consisting of a hydrogenation/dehydrogenation metal and an indium-containing non-acidic crystalline microporous material, under conditions including a temperature of from 800° F. to 1100° F., a pressure of about 0 to 500 psig, and LHSV of 0.1 to 20; and cofeeding with said feedstream a mixture of hydrogen and diluent which is inert to aromatization under the conditions of the process wherein the hydrogen:hydrocarbon (feed) ratio (molar) ranges from 0.1 to 20 and wherein the diluent hydrocarbon (feed) ratio (molar) ranges from 1 to 20;

and recovering a reformate of octane number and aromatic content greater than that of the feedstream and greater than that of the reformate produced in the absence of said diluent.

29. The process of claim 28, wherein the diluent is at least one hydrocarbon of 1 to 5 carbon atoms.

30. The process of claim 28, wherein the diluent is an aromatic.

31. The process of claim 28, wherein at least a portion of the reformate is recycled as diluent in said cofeeding.

32. The process of claim 28, wherein the naphtha is hydrotreated prior to reforming.

33. The process of claim 28, wherein the crystalline microporous material is characterized by a pore size the average diameter of which ranges from about 5 to about 8 Angstroms.

34. The process of claim 28, wherein the crystalline microporous material is isostructural to ZSM-5.

35. The process of claim 28, wherein said metal is platinum.

36. The process of claim 34, wherein said metal is platinum.

37. The process of claim 28, wherein said crystalline microporous material is isostructural with a zeolite.

38. The process of claim 37, wherein said zeolite is ZSM-5, ZSM-11, ZSM-12, ZSM-20, ZSM-23, ZSM-48 and ZSM-50.

39. The process of claim 28, wherein said crystalline microporous material is a SAPO or an ALPO.

40. The process of claim 28, wherein said crystalline microporous material is bound with silica.

41. The process of claim 28, wherein the diluent is nitrogen, helium, carbon dioxide.

42. The process of claim 28, wherein the diluent is predominantly propane and the hydrogen:hydrocarbon (feed) ratio (molar) is less than 3:1 and the reactor total pressure is less than 150 psig.

43. A process for reforming naphthas comprising
providing a feedstream which is a $C_6^+$ paraffin rich naphtha;
contacting the feedstream with a catalyst comprising a reforming hydrogenation/dehydrogenation metal and an indium containing non-acidic crystalline microporous material, under reforming conditions, and to increase the octane of the reformate produced and its aromatic content.

44. The process of claim 43, wherein said diluent is a $C_1$-$C_5$ hydrocarbon.

45. The process of claim 43, wherein the diluent is methane, ethane, propane, butane, isobutane, pentane, and combinations thereof.

46. The process of claim 43, wherein the diluent is helium, nitrogen, or carbon dioxide.

47. The process of claim 43, wherein the naphtha is hydrotreated prior to reforming.

48. The process of claim 43, wherein the crystalline microporous material is characterized by a pore size the average diameter of which ranges from about 5 to about 8 Angstroms.

49. The process of claim 43, which further includes recovering hydrogen.

50. The process of claim 43, wherein said crystalline microporous material is isostructural with a zeolite.

51. The process of claim 47, wherein said zeolite is ZSM-5.

52. The process of claim 43, wherein said crystalline microporous material is isostructural with a SAPO or ALPO.

53. A method for increasing the aromatic content of a reformate with a research octane in the range of 50 to 90 comprising
providing said reformate of research octane of 50 to 90 containing $C_6^+$ aliphatics and contacting said reformate with a catalyst composition, at a temperature of at least about 800° F., at a pressure ranging from about 0 to about 500 psig, and at a liquid hourly space velocity (LHSV) ranging from 0.1 to 20; wherein said catalyst composition comprises a hydrogenation/dehydrogenation component and an indium containing non-acidic crystalline, microporous material;
producing a product of research octane greater than that of the reformate and of aromatic components content greater than that of the reformate.

54. The method of claim 53, wherein the hydrogenation/dehydrogenation metal is platinum.

55. The method of claim 53, wherein the hydrogenation/dehydrogenation metal is selected from the group consisting of platinum, palladium, rhodium, rhenium, and mixtures thereof.

56. The method of claim 53, the reformate of research octane of 50 to 90 which contains $C_6$ and $C_7$ paraffins, which on contact with said catalyst are aromatized to $C_{6+}$ aromatics.

57. The method of claim 53, further including increasing the liquid yield of reforming, by contacting a naphtha, under reforming conditions, with an acidic reforming catalyst to produce said reformate of research octane of 50 to 90 and containing said $C_6^+$ aliphatics, and then undertaking said contacting.

58. The method of claim 53, wherein providing said reformate comprises contacting naphtha fraction under reforming conditions of temperature and pressure with a reforming catalyst which is effective to provide a reformate of 50 to 90 research octane containing a $C_{6+}$ paraffin fraction.

59. The process of claim 58, wherein said $C_{6+}$ paraffin fraction includes $C_6$ to $C_{10}$ paraffins.

60. The method of claim 53, wherein the non-acidic microporous crystalline material exhibits the X-ray diffraction pattern of a zeolite selected from the group consisting of ZSM-5, ZSM-11, ZSM-12, ZSM-20, ZSM-23, ZSM-48, ZSM-50, and zeolite beta.

61. The process of claim 60, wherein the non-acidic, microporous crystalline material contains less than 0.1 weight percent aluminum.

62. The process of claim 53, wherein the non-acidic, microporous crystalline material is a SAPO or an ALPO.

63. The method of claim 53, wherein the non-acidic crystalline microporous material exhibits the X-ray diffraction pattern of ZSM-5.

64. The method of claim 53, wherein the non-acidic microporous material exhibits the X-ray diffraction pattern of ZSM-11.

65. The method of claim 53, wherein the dehydrogenation metal is a Group VIII metal.

66. The method of claim 53, wherein the dehydrogenation metal is a platinum group metal.

* * * * *

UNITED STATES PATENT AND TRADEMARK OFFICE
CERTIFICATE OF CORRECTION

PATENT NO. : 5,013,423

DATED : May 7, 1991

INVENTOR(S) : Nai Yuen Chen, et al

It is certified that error appears in the above-identified patent and that said Letters Patent is hereby corrected as shown below:

Column 28, line 6 (claim 10) "ZSM 50" should read --ZSM-50--.

Signed and Sealed this

Twenty-fourth Day of November, 1992

*Attest:*

DOUGLAS B. COMER

*Attesting Officer*  Acting Commissioner of Patents and Trademarks